(12) United States Patent
Cunningham et al.

(10) Patent No.: US 8,003,594 B2
(45) Date of Patent: Aug. 23, 2011

(54) FOAMABLE MOISTURIZING COMPOSITIONS

(75) Inventors: Corey Cunningham, Larsen, WI (US); Philip Kieffer, Neenah, WI (US); Jeffery Seidling, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 921 days.

(21) Appl. No.: 11/797,204

(22) Filed: Apr. 30, 2007

(65) Prior Publication Data

US 2008/0268188 A1   Oct. 30, 2008

(51) Int. Cl.
*C11D 3/00* (2006.01)
*B67D 7/76* (2010.01)
*A61K 8/02* (2006.01)

(52) U.S. Cl. .................. 510/504; 222/190; 424/401
(58) Field of Classification Search .................. 222/190; 510/504; 424/401
See application file for complete search history.

(56) References Cited

U.S. PATENT DOCUMENTS

| | | | |
|---|---|---|---|
| 4,876,083 A | | 10/1989 | Grollier et al. |
| 5,508,454 A | | 4/1996 | Brancq et al. |
| 5,523,078 A | * | 6/1996 | Baylin .................. 424/70.1 |
| 5,824,324 A | * | 10/1998 | Cettina et al. .................. 424/401 |
| 6,053,364 A | * | 4/2000 | van der Heijden ......... 222/145.6 |
| 6,242,412 B1 | | 6/2001 | Chambers et al. |
| 6,306,411 B1 | * | 10/2001 | Jager Lezer .................. 424/401 |
| 6,329,353 B1 | | 12/2001 | Dalrymple et al. |
| 6,660,282 B2 | * | 12/2003 | Crotty et al. .................. 424/401 |
| 2005/0049157 A1 | | 3/2005 | MacDonald et al. |
| 2005/0058674 A1 | | 3/2005 | Joseph et al. |
| 2005/0189377 A1 | * | 9/2005 | Lanzendorfer et al. ........... 222/1 |
| 2005/0222001 A1 | * | 10/2005 | Baumeister et al. .......... 510/123 |

FOREIGN PATENT DOCUMENTS

| | | |
|---|---|---|
| DE | 102005035398 A1 | 2/2007 |
| EP | 0166232 A2 | 1/1986 |
| EP | 0775510 A2 | 5/1997 |
| WO | 91/14759 | 10/1991 |

OTHER PUBLICATIONS

"Wacker-Belsil DMC 6038: Bis-PEG 16-Methyl Ether Dimethicone" Wacker Silicones: Product Specification, [Online], Aug. 29, 2003 (www.essentialingredients.com/PDF/SPECS_dmc6038.pdf).
(PCT/IB2008/050816) International Search Report—4 pages.

\* cited by examiner

*Primary Examiner* — Milton I Cano
*Assistant Examiner* — Thuy-Al N Nguyen
(74) *Attorney, Agent, or Firm* — Dority & Manning, P.A.

(57) ABSTRACT

Foamable moisturizing compositions are disclosed. The compositions can include quaternary ammonium surfactant, humectant, secondary solubilizer, and thickening agent. In one embodiment, the composition can be contained in a non-aerosol dispensing container that mixes the composition with air causing the composition to foam when dispensed.

17 Claims, 1 Drawing Sheet

FOAMABLE MOISTURIZING COMPOSITIONS

BACKGROUND

Recently, consumer foamable moisturizers have appeared on the market. Foamable moisturizers are typically kept in a dispensing container that mixes the moisturizing composition with air when dispensed to form foam. Lotions have been formulated as leave-on foams, for example, to increase the enjoyment children find in moisturizing in a manner that is more entertaining and less messy than using a traditional emulsion product.

However, such moisturizing leave-on foams often contain a high level of active ingredients. In addition, such moisturizing foams typically consist of two phases, an oil phase and a water phase, thereby requiring special heating and cooling steps during production. Two phase moisturizers also have product shelf life concerns. For example, such two phase moisturizers often include a "shake well" label on packaging which can impact convenience, consumer appeal, and the like.

In view of the above, a need currently exists for an improved foamable moisturizing composition. In particular, a need exists for a foamable moisturizing composition containing a low level of active ingredients. A need also exists for a leave-on moisturizing foam that is a single phase aqueous composition containing no dispersed oil phase.

SUMMARY

In general, the present disclosure is directed to foamable moisturizing compositions. For example, in one embodiment, the foamable moisturizing composition includes a quaternary ammonium surfactant, a humectant, a secondary solubilizer, and a thickener. The quaternary ammonium surfactant, humectant, secondary solubilizer, and thickener can form a single phase.

In still another embodiment of the present disclosure, the foamable moisturizing composition as described above is dispensed from a dispensing container. The dispensing container may include a non-aerosol pumping device configured to combine the moisturizing composition with air. For instance, the pumping device may include an air pump and a liquid pump that are both in communication with an actuating head. Displacing the actuating head manually causes the air pump to pump air and the liquid pump to pump the moisturizing composition into a mixing chamber for forming a foam as the composition is dispensed.

Other features and aspects of the present disclosure are discussed in greater detail below.

BRIEF DESCRIPTION OF THE DRAWINGS

A full and enabling disclosure of the present disclosure, including the best mode thereof, directed to one of ordinary skill in the art, is set forth more particularly in the remainder of the specification, which makes reference to the following figures.

Figure 1:
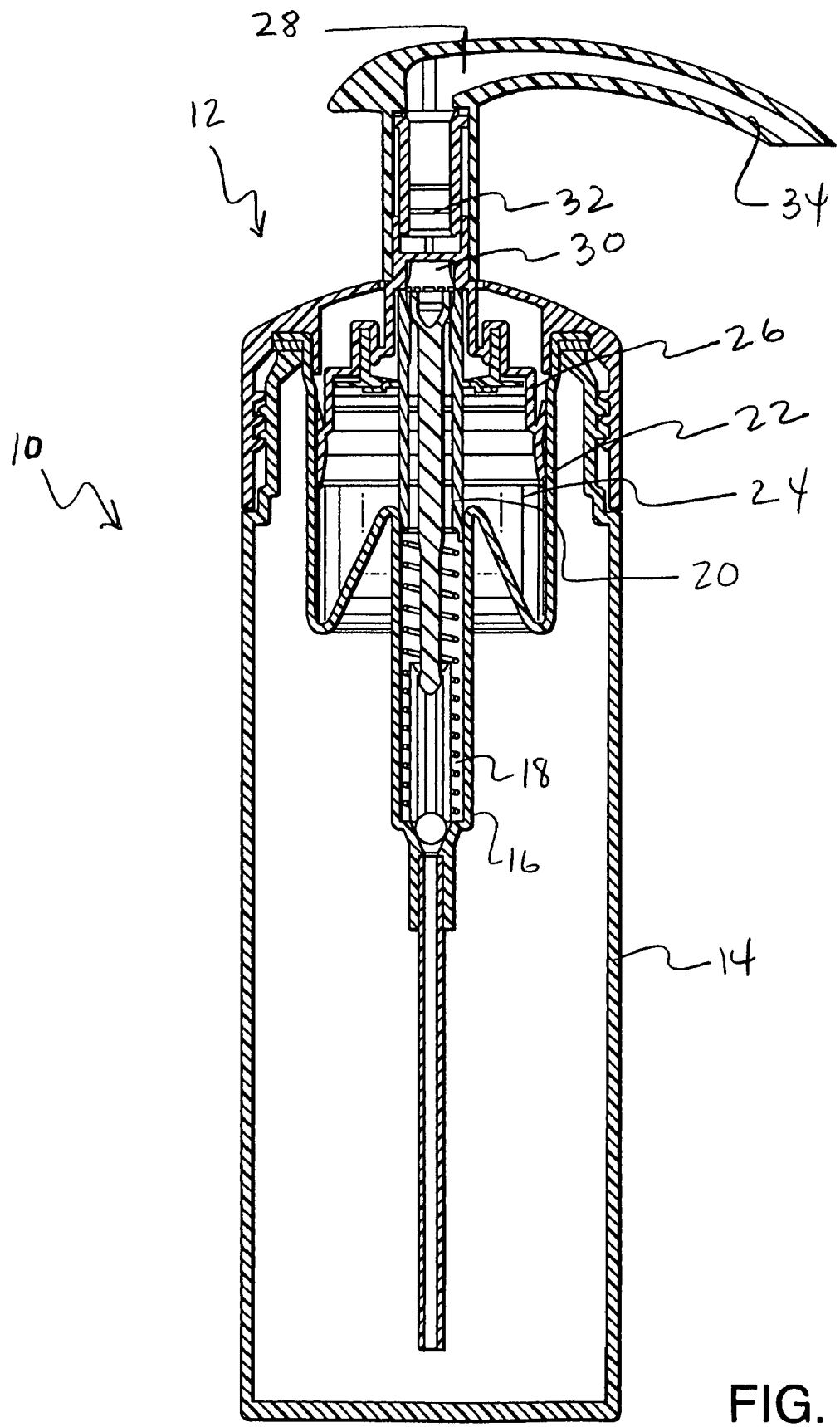
FIG. 1 is a cross-sectional view of one embodiment of a dispensing container that may be used in accordance with the present disclosure.

Repeat use of reference characters in the present specification and drawings is intended to represent same or analogous features or elements of the disclosure.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to a foamable leave-on moisturizing composition. The composition, for instance, can contain a single phase aqueous composition containing no dispersed oil phase. The composition can also contain a low level of active ingredients, if desired.

In this regard, liquid-gas foams are composed of gas cells surrounded by a liquid. The gas cells are films of liquid (lamellae) surrounding the gas bubble with the planar faces of liquid films meeting at angular intersections called Plateau junctions. To be mechanically stable, the lamellae of three bubbles meeting must be at an angle of 120°. With the addition of more bubbles to the foam, the perfect angle for mechanical stability is lost and the bubbles take on a more polygonal type of network. In a three dimensional gas cell within a foam, the resulting cell is polyhedral in nature.

A liquid-gas foam can be considered an emulsion with the liquid being the continuous phase and the dispersed phase composed of gas bubbles. Surfactants are frequently used to form most foams. The surfactants reduce the surface tension of the liquid phase and stabilize the films against rupture. The polar heads of the surfactants arrange themselves within the polar liquid and the hydrophobic tails project out into the air if the bubble is on the outside of the film, or into the Plateau junction if the bubble is within the film.

Liquid-gas foams can be categorized into dry and wet foams. In a dry foam, there is very little liquid (less than 1% by volume) and it exists in very thin films. The junctions of these films can be visualized in terms of a thin line with no discernable width. The polyhedral nature of the gas cell is clearly visible and very little fluid is maintained within the foam making this foam fairly stable.

A foam containing a percent or more of liquid is considered a wet foam. Liquid accumulates in the Plateau borders of these foams causing them to increase in width. Due to the swelling of the Plateau junctions, the corners and edges of the polyhedral cell are rounded off. Pressure differences between adjacent cells and gravity force liquid from these foams passing the liquid through the Plateau junctions (drainage) to the substrate until the lower-energy dry foam is reached or the bubble ruptures. However, with increased liquid, the cells regain their spherical nature and the foam degrades into a bubbly liquid.

For a liquid to foam with any degree of success, it must be able to expand its surface area to form a membrane around gas bubbles, possess the correct rheological and surface properties to reduce the thinning of the lamellae leading to bubble coalescence, and slow the diffusion of gas across lamellae from small to large bubbles or to the surrounding atmosphere.

In this regard, the present disclosure is directed to an improved foamable moisturizing composition. In accordance with the present disclosure, the foamable leave-on moisturizing composition can be a combination of quaternary ammonium surfactant, humectant, secondary solubilizer, and thickener. The present inventors have discovered that such a combination results in a single phase aqueous composition containing no dispersed oil phase. Of particular advantage, the moisturizing composition of the present disclosure can be used to teach good moisturizing habits to toddlers in a manner that is more entertaining and less messy than traditional emulsion lotion products. Furthermore, such a composition can contain a low level of active ingredients if desired and requires no special heating or cooling steps during production.

A low level of active ingredients may be desirable for several reasons. A low level of active ingredients can reduce the cost of producing the moisturizing compositions of the present disclosure. Additionally, in some instances, certain active ingredients can act as irritants. Whereas traditional foaming compositions are often associated with rinse-off products, the foamable composition of the present disclosure is particularly suited for a leave-on moisturizing composition. As such, a low level of active ingredients can be beneficial for such a leave-on composition.

Foamable moisturizing compositions made in accordance with the present disclosure can be used in various different applications and for various different purposes. For example, in one embodiment, the moisturizing composition can be formulated for everyday use by consumers. For instance, the foamable moisturizing composition can be used to moisturize one's body.

The moisturizing composition of the present disclosure is also well suited for use by toddlers. In particular, the foamable composition may be used by parents, teachers and other caregivers for teaching proper moisturizing to toddlers. The foaming action of the moisturizing composition makes the experience fun and interactive for toddlers and young children and increases the likelihood that they will want to repeat the experience without being told or instructed.

As described above, the moisturizing composition of the present disclosure generally contains a quaternary ammonium surfactant in combination with other compounds. In general, any suitable quaternary ammonium surfactant can be utilized. For instance, in one embodiment, the quaternary ammonium surfactant may comprise palmitamidopropyltrimonium chloride. In some embodiments of the present disclosure, cocamidopropyltrimonium chloride can be utilized as a suitable quaternary ammonium surfactant. In other embodiments of the present disclosure, other suitable x-amidopropyltrimonium chlorides can be utilized as quaternary ammonium surfactants where x is a carbon chain length of from about 10 to about 20.

In still other embodiments, suitable quaternary ammonium surfactants can include cocodimonium hydroxypropyl hydrolyzed proteins, cocodimonium hydroxypropyl hydrolyzed rice protein, cocodimonium hydroxypropyl hydrolyzed silk protein, cocodimonium hydroxypropyl hydrolyzed soy protein, palmitamidopropyltrimonium chloride, and silicone quaternium-8.

The amount of quaternary ammonium surfactant contained within the moisturizing composition of the present disclosure may depend upon various factors. For instance, the amount of quaternary ammonium surfactant contained in the composition may depend upon the desired use for the composition. However, the present disclosure contemplates a low level of active ingredients in the composition. In general, a quaternary ammonium surfactant is present in the composition in an amount of at least 0.5 percent by weight. For instance, the quaternary ammonium surfactant can be present in the composition in an amount from about 0.5 percent to about 5 percent by weight, such as from about 0.7 percent to about 3 percent by weight. Of particular advantage, the quaternary ammonium surfactant provides the composition with a conditioning foam. Additionally, such quaternary ammonium surfactants can be utilized at levels that do not illicit an irritation response in skin.

The humectant component of the moisturizing compositions of the present disclosure is generally present in an amount of from about 0.1% to about 10% by weight, such as from about 1% to about 5% by weight. Humectants are typically cosmetic ingredients used to increase the water content of the top layers of the skin or mucous membrane, by helping control the moisture exchange between the product, the skin, and the atmosphere. Humectants may include primarily hydroscopic materials. Suitable humectants for inclusion in the moisturizing and lubricating compositions of the present invention include urocanic acid, N-Acetyl ethanolamine, aloe vera gel, arginine PCA, chitosan PCA, copper PCA, Corn glycerides, dimethyl imidazolidinone, fructose, glucamine, glucose, glucose glutamate, glucuronic acid, glutamic acid, glycereth-7, glycereth-12, glycereth-20, glycereth-26, glycerin, honey, hydrogenated honey, hydrogenated starch hydrolysates, hydrolyzed corn starch, lactamide MEA, lactic acid, lactose lysine PCA, mannitol, methyl gluceth-10, methyl gluceth-20, PCA, PEG-2 lactamide, PEG-10 propylene glycol, polyamino acids, polysaccharides, polyamino sugar condensate, potassium PCA, propylene glycol, propylene glycol citrate, saccharide hydrolysate, saccharide isomerate, sodium aspartate, sodium lactate, sodium PCA, sorbitol, TEA-lactate, TEA-PCA, Urea, Xylitol, and the like and mixtures thereof. Preferred humectants include polyols, glycerin, ethoxylated glycerin, polyethylene glycols, hydrogenated starch hydrolysates, propylene glycol, silicone glycol, pyrrolidone carboxylic acid and mixtures thereof.

The secondary solubilizer can function as a surfactant while also providing stability to the foam produced utilizing the moisturizing composition of the present disclosure. Such a secondary solubilizer can help to enhance the appearance of dry or damaged skin and substantive materials which adhere to the skin to reduce flaking and restore suppleness. The secondary solubilizer can assist in building foam and adding body to foam. The secondary solubilizer can also serve to condition the foam in conjunction with the quaternary ammonium surfactant. Suitable secondary solubilizers can include bis-PEG-15 methyl ether dimethicone. Other suitable compounds can include bis-PEG-X methyl ether dimethicones where x is from about 6 to about 32. Still other suitable compounds can include silicone compounds such as ethoxylated-PEG-x dimethicone in which x is greater than or equal to 12.

Other suitable secondary solubilizers can include PEG-45 palm kernel glycerides, ethoxylated capric/caprylic glycerides, PEG-40 hydrogenated castor oil, polysorbate-20, coceth-7, dimethicone PEG-7 cocoate, PPG-1-PEG-9 lauryl glycol ether, dimethicone PEG-7 cocoate. In general, the secondary solubilizer is present in the composition in an amount of at least 0.1 percent by weight. For instance, the secondary solubilizer can be present in the composition in an amount from about 0.1 percent to about 2 percent by weight, such as from about 0.3 percent to about 1 percent by weight.

Thickeners that may be used in the composition include various modified celluloses. For instance, the thickener may comprise ethyl cellulose, hydroxyethyl cellulose, hydroxypropyl cellulose, carboxymethyl cellulose, hydroxypropyl methyl cellulose, hydroxyethyl methyl cellulose, and combinations thereof. Other thickeners include natural gums, such as guar gum, carrageenan, gum Arabic, locust bean gum, xanthan gum, and mixtures thereof. Other various polymeric thickeners that may be used include a polyether propanoic acid TMX copolymer or an acrylate polymer such as an alkyl acrylate crosspolymer containing from about 10 carbon atoms to about 30 carbon atoms in the alkyl chain. Still other thickeners can include clays such as bentonite, laponite, hectorite, magnesium aluminum silicate, and combinations thereof. Any such thickener can be used in combination with other thickeners as desired.

The moisturizing composition can also include water. The amount of water present in the composition may vary depending upon the particular application and the desired result. Water is generally present in the composition in an amount of at least 75 percent by weight, such as from about 75 percent to about 99 percent by weight. In one particular embodiment, for instance, water may be present in an amount from about 85 percent to about 97 percent by weight.

The moisturizing composition of the present disclosure may contain various other ingredients to impart desired characteristics to the composition. Examples of additives that may be added to the composition include detackifiers, fragrances, thickeners, emollients, suspended beads, organic sunscreens, dyes, preservatives, and the like.

For instance, detackifiers that may be used in the composition include various betaines. In some embodiments, the betaines can include a carbon chain that has a length of less than about 10. Suitable detackifiers can also include silicones (ethoxylated, propoxylated), hydrogenated oils/fatty acids, esters, and combinations thereof.

The moisturizing composition can also contain various emollients. In particular, water soluble or water compatible emollients are desirable in connection with the present application. Suitable emollients that can be used include ethoxylated and propoxylated alcohols, such as cetyl alcohols and ethoxylated lanolin, PEG esters, and glyceryl esters. In certain embodiments, the emollients would be a low level addition. In certain embodiments, oil soluble emollients can be used in amounts sufficient to keep a single phase.

Organic sunscreens that may be present in the composition include ethylhexyl methoxycinnamate, avobenzone, octocrylene, benzophenone-3, benzophenone-4, phenylbenzimidazole sulfonic acid, ethylhexyl salicylate, homosalate, oxybenzone, and mixtures thereof. In particular, water soluble or water compatible organic sunscreens are desirable in connection with the present application. In certain embodiments, organic sunscreens can be used in amounts sufficient to keep a single phase.

The moisturizing composition can also contain various preservatives to increase the shelf life of the composition. Some suitable preservatives that can be used in the present disclosure include, but are not limited to, Kathon CG®, which is a mixture of methylchloroisothiazolinone and methylisothiazolinone available from Rohm & Haas; Mackstat H 66 (available from McIntyre Group, Chicago, Ill.); DMDM hydantoin (e.g., Glydant Plus, Lonza, Inc., Fair Lawn, N.J.); tetrasodium EDTA; iodopropynyl butylcarbamate; benzoic esters (parabens), such as methylparaben, propylparaben, butylparaben, ethylparaben, isopropylparaben, isobutylparaben, benzylparaben, sodium methylparaben, and sodium propylparaben; 2-bromo-2-nitropropane-1,3-diol; benzoic acid; imidazolidinyl urea; diazolidinyl urea; and the like. Other suitable preservatives include those sold by Sutton Labs, such as "Germall 115" (amidazolidinyl urea), "Germall II" (diazolidinyl urea), "Germall Plus" (diazolidinyl urea and iodopropynyl butylcarbonate), phenoxyethanol, and disodium EDTA.

The amount of the preservative utilized in the moisturizing composition can generally vary depending on the relative amounts of the other components present within the formulation. For example, in some embodiments, the preservative is present in the formulation in an amount between about 0.001% to about 5% by weight, in some embodiments between about 0.001 to about 1% by weight, and in some embodiments, between about 0.1% to about 0.15% by weight of the formulation.

Still other optional ingredients that may be included in the moisturizing composition include, but are not limited to, anti-microbial agents, antioxidants (product integrity); anti-reddening agents, such as aloe extract; astringents—cosmetic (induce a tightening or tingling sensation on skin); astringents—drug (a drug product which checks oozing, discharge, or bleeding when applied to skin or mucous membrane and works by coagulating protein); biological additives (enhance the performance or consumer appeal of the product); deodorants (reduce or eliminate unpleasant odor and protect against the formation of malodor on body surfaces); external analgesics (a topically applied drug that has a topical analgesic, anesthetic, or antipruritic effect by depressing cutaneous sensory receptors, of that has a topical counterirritant effect by stimulating cutaneous sensory receptors); film formers (to hold active ingredients on the skin by producing a continuous film on skin upon drying); hydrotropes (helps dissolve some anti-microbial agents); opacifiers (reduce the clarity or transparent appearance of the product); skin conditioning agents; skin exfoliating agents (ingredients that increase the rate of skin cell turnover such as alpha hydroxy acids and beta hydroxyacids); skin protectants (a drug product which protects injured or exposed skin or mucous membrane surface from harmful or annoying stimuli); natural moisturizing factors, amino acids, and the like. Other suitable optional ingredients can include urea, ceramides, hyaluronic acid, cholesterol, fatty acids, triglycerides, phospholipids, glycosphingolipids, amino acids, glycosaminoglycans, mucopolysaccharide, and the like. All such optional ingredients can be used in combination with other such optional ingredients as desired.

The moisturizing composition may be prepared in any conventional manner, e.g. by simply admixture of the components. For instance, in one embodiment, all of the ingredients can be added and mixed together at the same time.

The moisturizing composition is foamable in that the composition is specifically formulated to form a foam when aerated. For example, in one embodiment, the composition may be contained in an aerosol container. In an aerosol container, the composition is maintained under pressure sufficient to cause foam formation when dispensed.

Of particular advantage, however, the moisturizing composition of the present disclosure is foamable without the necessity of being placed in an aerosol container. For instance, in an alternative embodiment, the composition may be contained in a manual dispensing foam pump container. The non-aerosol container, for instance, may entrain air in the foamable composition as it is dispensed.

For instance, referring to FIG. 1, one embodiment of a dispensing container generally 10 that may be used with the moisturizing composition is illustrated. The dispensing container 10 includes a dispensing assembly 12 that is screwed onto a liquid container 14. The dispensing assembly 12 includes a liquid pump 16 that comprises a liquid pump chamber 18 and a liquid pump piston 20. The dispensing container further includes an air pump 22 with an air pump chamber 24 and an air pump piston 26. The liquid piston 20 and the air piston 26 are coupled to an actuating head 28.

In order to dispense a foam from the dispensing container 10, the actuating head 28 is displaced by being pressed downwardly causing the pistons 20 and 26 to move downwards as well. As the pistons 20 and 26 are moved downwards, the volumes of the chambers 18 and 24 are reduced causing air and liquid to enter a mixing chamber 30. The liquid and air mixture then passes through a screen or mesh 32 and into a dispenser 34.

After foam is dispensed through the dispenser 34, the actuating head 28 is released and thus returns to its initial position.

The present disclosure may be better understood with respect to the following examples which describe formulations in accordance with the present disclosure.

Example 1

| Trade Name | INCI | Description | % weight |
| --- | --- | --- | --- |
| Varisoft PATC | Palmitamidopropyl-trimonium Chloride | quaternary ammonium surfactant | 1.00 |
| Glycerin | Glycerin | humectant | 2.00 |
| Wacker DMC 6038 | Bis-PEG-15 Methyl Ether Dimethicone | secondary solubilizer | 0.50 |
| Natrosol HHX Pharm | Hydroxyethylcellulose | thickener | 0.05 |
| Water | Water/Aqua | | 96.45 |

Example 2

| Trade Name | INCI | Description | % weight |
| --- | --- | --- | --- |
| Varisoft PATC | Palmitamidopropyl-trimonium Chloride | quaternary ammonium surfactant | 1.00 |
| Glycerin | Glycerin | humectant | 2.00 |
| Wacker DMC 6038 | Bis-PEG-15 Methyl Ether Dimethicone | secondary solubilizer | 0.50 |
| Betafin BP-20 | Betaine | detackifier | 1.50 |
| Natrosol HHX Pharm | Hydroxyethylcellulose | thickener | 0.05 |
| Water | Water, Aqua | | 94.95 |

Example 3

| Trade Name | INCI | Description | % weight |
| --- | --- | --- | --- |
| Varisoft PATC | Palmitamidopropyl-trimonium Chloride | quaternary ammonium surfactant | 1.00 |
| Glycerin | Glycerin | humectant | 2.00 |
| Wacker DMC 6038 | Bis-PEG 15-Methyl Ether Dimethicone | secondary solubilizer | 0.50 |
| Betafin BP-20 | Betaine | detackifier | 1.50 |
| Natrosol HHX Pharm | Hydroxyethylcellulose | thickener | 0.05 |
| Paragon MEPB | Phenoxyethanol, Methylparaben, Ethylparaben, Propylparaben, Butylparaben | Preservative | 0.50 |
| Disodium EDTA | Disodium EDTA | Preservative | 0.05 |
| Water | Water/Aqua | | 94.40 |

Example 4

| Trade Name | INCI | Description | % weight |
| --- | --- | --- | --- |
| Varisoft PATC | Palmitamidopropyl-trimonium Chloride | quaternary ammonium surfactant | 1.00 |
| Glycerin | Glycerin | humectant | 2.00 |
| Wacker DMC 6038 | Bis-PEG 15-Methyl Ether Dimethicone | secondary solubilizer | 0.50 |
| Betafin BP-20 | Betaine | detackifier | 1.50 |
| Natrosol HHX Pharm | Hydroxyethylcellulose | thickener | 0.05 |
| Paragon MEPB | Phenoxyethanol, Methylparaben, Ethylparaben, Propylparaben, Butylparaben | Preservative | 0.50 |
| Disodium EDTA | Disodium EDTA | Preservative | 0.05 |
| D&C Blue 1 | Blue 1 | Dye | 0.7 |
| D&C Green 3 | Green 3 | Dye | 0.03 |
| Water | Water/Aqua | | 93.67 |

Example 5

| Trade Name | INCI | Description | % weight |
| --- | --- | --- | --- |
| Varisoft PATC | Palmitamidopropyl-trimonium Chloride | quaternary ammonium surfactant | 1.00 |
| Glycerin | Glycerin | humectant | 2.00 |
| Wacker DMC 6038 | Bis-PEG 15-Methyl Ether Dimethicone | secondary solubilizer | 0.50 |
| Laponite XLG | Sodium Magnesium Silicate | thickener | 0.05 |
| Water | Water/Aqua | | 96.45 |

These and other modifications and variations to the present disclosure may be practiced by those of ordinary skill in the art, without departing from the spirit and scope of the present disclosure, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the disclosure so further described in such appended claims.

What is claimed:

1. A foaming moisturizing product comprising:
    a dispensing container, wherein the dispensing container includes a non-aerosol pumping device, and
    a foamable moisturizing composition contained within the dispensing container, wherein the foamable moisturizing composition comprises a single aqueous liquid phase within the container and wherein the liquid phase is consisting essentially of a quaternary ammonium surfactant, said humectant, said secondary solublizer, said thickener, and optionally a preservative, a detackifier, a fragrance and natural moisturizing factors, and
    wherein the pumping device of the dispensing container is configured to combine the moisturizing composition with air when dispensed from the container for producing a foam.

2. A foaming moisturizing product as defined in claim 1, wherein the pumping device comprises an air pump and a liquid pump in communication with an actuating head, and wherein displacing the actuating head manually causes the liquid pump to pump moisturizing composition and the air pump to pump air for mixing with the moisturizing composition and forming a foam that is dispensed from the container.

3. A foaming moisturizing product as defined in claim 1, wherein said quaternary ammonium surfactant is present in the composition in an amount from about 0.5 percent to about 5 percent by weight.

4. A foaming moisturizing product as defined in claim 1, wherein said quaternary ammonium surfactant comprises x-amidopropyltrimonium chloride where x is a carbon chain length of from about 10 to about 20.

5. A foaming moisturizing product as defined in claim 1, wherein said quaternary ammonium surfactant comprises palmitamidopropyltrimonium chloride.

6. A foaming moisturizing product as defined in claim 1, wherein said quaternary ammonium surfactant is present in the composition in an amount from about 0.7 percent to about 3 percent by weight.

7. A foaming moisturizing product as defined in claim 1, wherein said humectant comprises glycerin.

8. A foaming moisturizing product as defined in claim 1, wherein said humectant is present in the composition in an amount from about 0.1 percent to about 10 percent by weight.

9. A foaming moisturizing product as defined in claim 1, wherein said secondary solubilizer comprising bis-PEG-X methyl ether dimethicone where x is from about 6 to about 32.

10. A foaming moisturizing product as defined in claim 1, wherein said secondary solubilizer comprising bis-PEG-15 methyl ether dimethicone.

11. A foaming moisturizing product as defined in claim 1, wherein said secondary solubilizer is present in the composition in an amount from about 0.1 percent to about 2 percent by weight.

12. A foaming moisturizing product as defined in claim 1, wherein said thickener comprises laponite.

13. A foaming moisturizing product as defined in claim 1, wherein said thickener comprises hydroxyethylcellulose.

14. A foaming moisturizing product as defined in claim 1, wherein a preservative is present.

15. A foaming moisturizing product as defined in claim 1, wherein a detackifier is present.

16. A foaming moisturizing product as defined in claim 1, wherein a fragrance is present.

17. A foaming moisturizing product as defined in claim 1, wherein natural moisturizing factors is present.

* * * * *